United States Patent
Kuper et al.

(10) Patent No.: US 6,680,072 B1
(45) Date of Patent: Jan. 20, 2004

(54) METHOD FOR PRODUCING MEDICAMENTS FROM PLANT EXTRACTS, IN A SOLID FORM OF ADMINISTRATION

(75) Inventors: Willi Kuper, Bross-Rohrheim (DE); Panagiotis Maidonis, Darmstadt (DE)

(73) Assignee: Steigerwald Arzneimitelwerk GmbH, Darmstadt (DE)

( * ) Notice: Subject to any disclaimer, the term of this patent is extended or adjusted under 35 U.S.C. 154(b) by 0 days.

(21) Appl. No.: 09/856,651
(22) PCT Filed: Nov. 24, 1999
(86) PCT No.: PCT/DE99/03767
§ 371 (c)(1), (2), (4) Date: Jul. 9, 2001
(87) PCT Pub. No.: WO00/30605
PCT Pub. Date: Jun. 2, 2000

(30) Foreign Application Priority Data

Nov. 24, 1998 (DE) .......................... 198 55 287
Nov. 24, 1998 (DE) .......................... 199 57 472

(51) Int. Cl.[7] .......................... A61K 9/14; A61K 9/16; A61K 9/20
(52) U.S. Cl. .................... 424/489; 424/490; 424/464; 424/465; 424/725
(58) Field of Search .................. 424/489, 490, 424/464, 465, 725

(56) References Cited

U.S. PATENT DOCUMENTS

| | | | | |
|---|---|---|---|---|
| 4,599,328 A | * | 7/1986 | Yamatsu et al. | 514/106 |
| 5,017,613 A | * | 5/1991 | Aubert et al. | 514/557 |
| 5,965,162 A | * | 10/1999 | Fuisz et al. | 424/441 |

* cited by examiner

*Primary Examiner*—Thurman K. Page
*Assistant Examiner*—Amy E Pulliam
(74) *Attorney, Agent, or Firm*—Wood, Phillips, Katz, Clark & Mortimer

(57) ABSTRACT

A dry extract is reduced in volume by compacting to produce a solid form of pharmaceutical such as a tablet or capsule containing plant extracts. The particles of compacted matter are subsequently screened to a uniform grain size, masked with titanium dioxide, talc, and highly dispersed silicon dioxide in a first mixing process, and treated with additional adjuvants in two more mixing steps.

The masked compacted matter has the flowability required for making tablets and is protected against moisture absorption. The extract portion is a minimum of 65 percent by weight, which allows for producing relatively small tablets that have low disintegration times due to masking.

6 Claims, No Drawings

METHOD FOR PRODUCING MEDICAMENTS FROM PLANT EXTRACTS, IN A SOLID FORM OF ADMINISTRATION

This invention relates to a method for producing pharmaceuticals in a solid form of application that contain plant extracts, in particular, St. John's wort extract.

The advantage of solid forms of pharmaceuticals such as tablets or capsules as compared to liquid forms of application is that they act in more downstream sections of the intestinal duct. This facilitates a more controlled release of the active ingredients and therefore better therapeutic control. The doctor can exactly dose each individual dose administered to treat a patient as required. In addition, solid pharmaceuticals are extremely stable and easily packaged, stored and transported.

An unsatisfactory aspect about administering tablets or capsules containing plant extracts, however, is that they are characterized by a large portion of adjuvants combined with relatively small portions of pharmaceutically active plant extracts so that their absorption and active agent concentrations at the absorption site are rather low. Furthermore, these tablets are comparatively large which makes it difficult for patients to swallow them.

DE 197 00 788 A1 disclosed a pharmaceutical based on St. John's wort extract that can be administered orally in dried form as a powder, granulate, capsule, or tablet. This document, however, does not reveal any engineering instructions as to how a tablet that is highly enriched with plant extract should be manufactured.

DE 196 39 375 A1 describes a dry mistletoe extract that is to be used as a powder or granulate in a capsule or tablet, or as a liquid. In particular, this invention suggests oral administration of a granulate containing calcium carbonate or saccharide.

A similar form of application is known from DE 196 27 376 A1 for a pharmaceutical based on an artichoke extract.

The pharmaceuticals mentioned above all share the disadvantage that they do not represent forms of application highly enriched with dried plant extract. This means that multiple tablets or a tablet so big that it cannot be swallowed would have to be administered if the dosage of the pharmaceutical is sufficiently high.

DE 36 16 054 A1 claims a homeopathic pharmaceutical. To produce this pharmaceutical, triturations of pig's bone marrow, pig's articular cartilage, gelatin and harpagophytins as well as an extremely high portion of adjuvants are granulated through a sieve. The granulate is cross-linked with more adjuvants and pressed into tablets. As this product has such a high portion of adjuvants, this method of manufacturing tablets from granulate cannot be used for tablets from plant extracts sized for oral application, which means tablets that are as low in adjuvants and as high in dried extract as possible.

A pharmaceutical preparation of extracts from various drugs known from DE 33 28 262 C 2 can be administered as a liquid or as a dry extract in the form of a powder, granulate, tablet, or capsule. In one of its embodiments, the powdered dry extract is mixed with lactose and magnesium stearate and pressed into tablets that are later granulated to yield the ready-for-use pharmaceutical preparation. In a second embodiment, the powdered dry extract is mixed with cellulose and magnesium stearate and immediately pressed into tablets. Although this patent describes solid forms of application that have a high portion of plant extracts, a tablet pressed in this way from a dry extract does not guarantee compliance with the parameters a pharmaceutical calls for, such as disintegration time and moisture protection.

JP 78 13 347 and JP 77 102 4416 each describe the manufacture of granulates produced from plant extracts by adding various adjuvants without specifically claiming conditions required for the industrial production of tablets containing a high portion of dry extract and meeting other requirements a conventional pharmaceutical would have to meet.

It is therefore the problem of this invention to propose a method for producing ready-made pharmaceuticals in a solid form of application whose active ingredient is a plant extract, and thereby to provide a galenically stable, highly effective pharmaceutical containing a large dose of extract in a comparatively small tablet that is easily dissolved and absorbed at the place of release.

This problem is solved according to the invention by a method comprising the characteristics described in claim 1.

In other words, it is the concept of the invention to compact a dry extract into granulate particles screened to a uniform size and to mask these particles in a mixing process with three layers of titanium dioxide, talc, and highly dispersed silicon dioxide. These granulate particles—compacted and masked with other adjuvants as may be required—are then further processed in the usual way to become tablets or capsules.

The combination of a compacting step, a screening to uniform grain size step, and a masking step as described yields a raw material that has good flow characteristics, an extremely high extract content, requires an accordingly smaller portion of adjuvants, and is therefore suited for the industrial manufacture of tablets and capsules. As the extract portion in the masked compacted matter is at least 65 percent by weight, a highly effective pharmaceutical based on plant extracts can be provided in typical tablet size. The adjuvants applied in the defined order when masking the granulate particles do not conflict with the efficacy of the pharmaceutical as the outer coat of highly disperse silicon dioxide prevents the granulate particles from melting into one another at their outer surfaces so that they disintegrate fast after intake and unfold their full efficacy.

In the three-step masking process, the titanium dioxide, which preferably is applied first, covers all surface areas of the granulate particles and provides moisture protection for the typically hygroscopic extract. The talc applied subsequently to the titanium dioxide coat fills any remaining spaces of the granulate surface to yield a smooth and continuous surface. Finally, the highly dispersed silicon dioxide as the outer coat acts as a separating layer between granulate particles in a pressed tablet. The granulate particles masked in this way are also characterized by good flowability, which is advantageous for further processing.

The subclaims and the subsequent description of an embodiment disclose other characteristics and advantageous improvements of the invention.

The method of the invention for producing tablets with plant extracts shall now be explained in more detail for the use of St. John's wort as an active ingredient for the treatment of depressions.

A liquid extract made of coarsely cut St. John's wort buds and flowertops using an ethanol-water mixture is evaporated to a viscid mass and in a step A converted by spray drying into a powdered dry extract to which specific adjuvants such as maltodextrin and highly dispersed silicon dioxide are added at a ratio of 9 to 1, amounting to a portion of 10 percent by weight of the dry plant extract. Other dextrins may be used alternatively.

In a step B, this dry extract is mechanically compacted into a granulate while adding lactose monohydrate as a binding agent. Alternative adjuvants such as lactose derivatives, cellulose derivatives, starch, mannitol, and calcium carbonate may be used in this step. A final screening process provides compacted matter with a uniform grain size and a maximum adjuvant portion of 15 percent by weight.

The still hygroscopic granulate with a homogeneous grain size is masked in a subsequent first of three mixing processes combined under step C first with titanium dioxide, then with talc, and finally with highly dispersed silicon dioxide to provide the tablets to be produced from the granulate with moisture protection, good flowability and good disintegration properties. The homogeneous grain size of the granulate ensures even and thin coating of all particles. In second and third mixing processes, the particles are further masked with lactose monohydrate and carbomethyl cellulose sodium, and then with magnesium stearate/stearic acid. The adjuvant portion now amounts to a maximum of 35 percent by weight. Alternatively, the adjuvants mentioned above can be used instead of lactose monohydrate, and sodium hydrogencarbonate, calcium carbonate, starch, pectin, magnesium oxide, potassium bicarbonate and potassium carbonate can be used for sodium carboxymethyl cellulose.

The good flow properties of the masked compacted particles make them suited for immediate processing in a tablet press (step D). The tablet pellets produced in this way are subsequently provided with a coat to protect them from light, oxygen, and moisture. The portion of dry plant extract is a minimum of 60 percent by weight after this. The tablet that can be produced in this way from plant extracts has good disintegration characteristics and facilitates high and accurate dosing of the St. Johns wort extract while being small in size and thus easy to swallow.

The invention is not limited to the embodiment described above. Various modifications regarding the dry extract and its production or the adjuvants used are conceivable within the framework of the concept of the invention, that is, producing a compactate of equally sized particles from dry extract that are subsequently masked with specific adjuvants and can be pressed to tablets with an extract portion between 65 and 75 percent by weight.

We claim:

1. A method for producing pharmaceuticals in a solid form from a liquid St. John's wort extract, the method comprising steps of:

a) converting a liquid St. John's wort extract into a dry extract, provided that at least one adjuvant is added during the conversion of the liquid extract into a dry extract;

b) compacting the dry extract into a granulate, provided that at least one substance is added during the compacting to improve granulation;

c) screening the compact granulate to a uniform size;

d) coating the compact granulate first with titanium dioxide, then with talc and then with highly dispersed silicon dioxide in that order; and e) pressing the compact and coated granulate into tablets.

2. The method according to claim 1 wherein lactose monohydrate is added as an adjuvant during the compacting of the dry extract.

3. The method according to claim 1 further comprising the step of treating the compact and coated granulate after step d) with at least one adjuvant to form a mixture suitable for forming a tablet.

4. The method according to claim 3 wherein the compact and coated granulate is first treated with lactose monohydrate and caboxymethyl cellulose sodium and then treated with magnesium stearate and stearic acid.

5. The method according to claim 1, 2, 3 or 4 wherein the amount of adjuvant to dry extract does not exceed 35 percent by weight.

6. The method according to claim 1, 2, 3 or 4 wherein the amount of adjuvant does not exceed 10 percent by weight during the production of the dry extract, does not exceed 5 percent during compacting, and does not exceed 20 percent by weight during the coating of the compact granulate with the titanium dioxide, talc and silicon dioxide.

* * * * *